(12) United States Patent
Borzooeian et al.

(10) Patent No.: US 11,079,387 B2
(45) Date of Patent: Aug. 3, 2021

(54) LENGTH-BASED CARBON NANOTUBE LADDERS

(71) Applicants: Zahra Borzooeian, Brighton, MA (US); Mohammad E. Taslim, Needham, MA (US)

(72) Inventors: Zahra Borzooeian, Brighton, MA (US); Mohammad E. Taslim, Needham, MA (US)

( * ) Notice: Subject to any disclaimer, the term of this patent is extended or adjusted under 35 U.S.C. 154(b) by 112 days.

(21) Appl. No.: 16/383,552

(22) Filed: Apr. 12, 2019

(65) Prior Publication Data

US 2019/0317102 A1 Oct. 17, 2019

Related U.S. Application Data

(60) Provisional application No. 62/656,645, filed on Apr. 12, 2018.

(51) Int. Cl.
*G01N 33/58* (2006.01)
*C01B 32/168* (2017.01)
*G01N 27/447* (2006.01)

(52) U.S. Cl.
CPC ......... *G01N 33/581* (2013.01); *C01B 32/168* (2017.08); *G01N 27/44726* (2013.01); *C01B 2202/02* (2013.01); *C01B 2202/06* (2013.01); *C01B 2202/34* (2013.01); *G01N 2550/00* (2013.01)

(58) Field of Classification Search
CPC ............ G01N 33/581; G01N 27/44726; C01B 32/168; C01B 2202/00; C01B 2202/02; C01B 2202/06; C01B 2202/34
USPC .................................................... 209/12.1
See application file for complete search history.

(56) References Cited

U.S. PATENT DOCUMENTS

| 4,555,490 | A | 11/1985 | Merril |
| 5,840,575 | A | 11/1998 | Hyman |
| 7,374,649 | B2 | 5/2008 | Jagota et al. |
| 10,060,910 | B2 * | 8/2018 | Coleman ......... G01N 33/54306 |
| 2004/0235016 | A1 | 11/2004 | Hamers et al. |

(Continued)

FOREIGN PATENT DOCUMENTS

WO WO-2008143281 A1 * 11/2008 ............. B01D 57/02

OTHER PUBLICATIONS

A. C. Dillon, Jones A, Bekkedahl T, Kiang C. Storage of hydrogen in single-walled carbon nanotubes. Nature. 1997;386:377-9.

(Continued)

*Primary Examiner* — Terrell H Matthews
(74) *Attorney, Agent, or Firm* — Nelson Mullins Riley & Scarborough LLP; Reza Mollaaghababa; Thomas J. Engellenner

(57) ABSTRACT

In one aspect, the present invention is generally directed to methods for measuring distribution of lengths of a collection of carbon nanotubes. In particular, the present teachings provide an indicator for length-based separation of carbon nanotubes (CNTs) via conjugation of one or more biomolecules onto the surfaces of the nanotubes. As discussed in more detail below, in some embodiments, such a method can include conjugating a biomolecule to the carbon nanotubes and subject the conjugated carbon nanotubes to silver-stained gel electrophoresis to separate the conjugated carbon nanotubes based on their lengths.

30 Claims, 1 Drawing Sheet

Step 1 — Carboxylating a collection of carbon nanotubes.

Step 2 — Covalently linking lysozyme to at least a portion of the carboxylated nanotubes.

Step 3 — Subjecting the lysozyme-conjugated carbon nanotubes to gel electrophoresis to separate the conjugated carbon nanotubes based on their lengths

(56) References Cited

U.S. PATENT DOCUMENTS

| | | | | |
|---|---|---|---|---|
| 2006/0024808 | A1* | 2/2006 | Darzins | C07K 16/00 |
| | | | | 435/195 |
| 2006/0142148 | A1* | 6/2006 | Ma | B01J 23/28 |
| | | | | 502/185 |
| 2007/0258880 | A1* | 11/2007 | Murakoshi | B82Y 30/00 |
| | | | | 423/447.1 |
| 2008/0076816 | A1* | 3/2008 | Bianco | B82Y 5/00 |
| | | | | 514/414 |
| 2010/0189626 | A1 | 7/2010 | Tanaka et al. | |
| 2011/0108424 | A1* | 5/2011 | Puget | B82Y 30/00 |
| | | | | 204/601 |
| 2012/0259098 | A1* | 10/2012 | Baker, Jr. | A61K 51/065 |
| | | | | 530/391.3 |
| 2012/0269721 | A1* | 10/2012 | Weng | G01N 33/54346 |
| | | | | 424/1.11 |
| 2014/0262972 | A1* | 9/2014 | Adiga | B41J 2/03 |
| | | | | 209/127.4 |
| 2018/0148479 | A1* | 5/2018 | Lim | C07K 14/005 |
| 2018/0243692 | A1 | 8/2018 | Borzooeian et al. | |
| 2019/0076075 | A1* | 3/2019 | Miller | A61B 5/14539 |
| 2020/0031672 | A1* | 1/2020 | Nihey | C01B 32/152 |
| 2020/0200706 | A1 | 6/2020 | Borzooeian et al. | |

OTHER PUBLICATIONS

Asuri P, Bale SS, Pangule RC, Shah DA, Kane RS, Dordick JS. Structure, function, and stability of enzymes covalently attached to single-walled carbon nanotubes. Langmuir. 2007 ;23 (24) : 12318-21.

Bachtold A, Hadley P, Nakanishi T, Dekker C. Logic circuits with carbon nanotube transistors. Science. 2001;294(5545):1317-20.

Bandow S, Rao A, Williams K, Thess A, Smalley R, Eklund P. Purification of single-wall carbon nanotubes by microfiltration. The Journal of Physical Chemistry B. 1997;101(44):8839-42.

Baughman RH, Zakhidov AA, de Heer WA. Carbon nanotubes—the route toward applications. science. 2002;297(5582):787-92.

Blum H, Beier H, Gross HJ. Improved silver staining of plant proteins, RNA and DNA in polyacrylamide gels. Electrophoresis. 1987;8(2):93-9.

Bonard JM, Stora T, Salvetat JP, Maier F, Stockli T, Duschl C, et al. Purification and size—selection of carbon nanotubes. Advanced Materials. 1997;9(10):827-31.

Chen P, Wu X, Lin J, Tan K. High H2 uptake by alkali-doped carbon nanotubes under ambient pressure and moderate temperatures. Science. 1999;285(5424):91-3.

Cheng J, Cheng SH. Influence of carbon nanotube length on toxicity to zebrafish embryos. International journal of nanomedicine. 2012;7:3731-9.

Coleman JN, Dalton A, Curran S, Rubio A, Davey A, Drury A, et al. Phase separation of carbon nanotubes and turbostratic graphite using a functional organic polymer. Advanced materials. 2000;12(3):213-6.

Dillon AC, Gennett T, Jones KM, Alleman JL, Parilla PA, Heben MJ. A simple and complete purification of single-walled carbon nanotube materials. Advanced Materials. 1999;11(16):1354-8.

Ding Z, Chen J, Gao S, Chang J, Zhang J, Kang E. Immobilization of chitosan onto poly-L-lactic acid film surface by plasma graft polymerization to control the morphology of fibroblast and liver cells. Biomaterials. 2004;25(6):1059-67.

Dong A, Caughey B, Caughey WS, Bhat KS, Coe JE. Secondary structure of the pentraxin female protein in water determined by infrared spectroscopy: Effects of calcium and phosphorylcholine. Biochemistry. 1992;31(39):9364-70.

Dong A, Huang P, Caughey WS. Redox-dependent changes in. beta.-extended chain and turn structures of cytochrome c in water solution determined by second derivative amide I infrared spectra. Biochemistry. 1992;31(1):182-9.

Doorn SK, Fields RE, Hu H, Hamon MA, Haddon RC, Selegue JP, et al. High resolution capillary electrophoresis of carbon nanotubes. Journal of the American Chemical Society. 2002;124(12):3169-74.

Doorn SK, Strano MS, O'Connell MJ, Haroz EH, Rialon KL, Hauge RH, et al. Capillary electrophoresis separations of bundled and individual carbon nanotubes. The Journal of Physical Chemistry B. 2003;107(25):6063-9.

Duesberg G, Blau W, Byrne H, Muster J, Burghard M, Roth S. Chromatography of carbon nanotubes. Synthetic Metals. 1999;103(1):2484-5.

Duesberg G, Muster J, Krstic V, Burghard M, Roth S. Chromatographic size separation of single-wall carbon nanotubes. Applied Physics A: Materials Science & Processing. 1998;67(1):117-9.

Franklin AD, Chen Z. Length scaling of carbon nanotube transistors. Nature nanotechnology. 2010;5(12):858-62.

Goux—Capes L, Filoramo A, Cote D, Bourgoin JP, Patillon JN. Coupling carbon nanotubes through DNA linker using a biological recognition complex. physica status solidi (a). 2006 ;203 (6): 1132-6.

He H, Pham-Huy LA, Dramou P, Xiao D, Zuo P, Pham-Huy C. Carbon nanotubes: applications in pharmacy and -medicine. BioMed research international. 2013;2013, 1-12.

Heller DA, Mayrhofer RM, Baik S, Grinkova YV, Usrey ML, Strano MS. Concomitant length and diameter separation of single-walled carbon nanotubes. Journal of the American Chemical Society. 2004;126(44):14567-73.

Holzinger M, Hirsch A, Bernier P, Duesberg G, Burghard M. A new purification method for single-wall carbon nanotubes (SWNTs). Applied Physics A. 2000;70(5):599-602.

Huang W, Taylor S, Fu K, Lin Y, Zhang D, Hanks TW, et al. Attaching proteins to carbon nanotubes via diimide-activated amidation. Nano Letters. 2002;2(4):311-4.

Kong J, Franklin NR, Zhou C, Chapline MG, Peng S, Cho K, et al. Nanotube molecular wires as chemical sensors. science. 2000;287(5453):622-5.

Li F, Cheng H, Xing Y, Tan P, Su G. Purification of single-walled carbon nanotubes synthesized by the catalytic decomposition of hydrocarbons. Carbon. 2000;38(14):2041-5.

Liu C, Fan Y, Liu M, Cong H, Cheng H, Dresselhaus MS. Hydrogen storage in single-walled carbon nanotubes at room temperature. Science. 1999;286(5442):1127-9.

Liu J, Rinzler AG, Dai H, Hafner JH, Bradley RK, Boul PJ, et al. Fullerene pipes. Science. 1998;280(5367):1253-6.

Niyogi S, Hu H, Hamon M, Bhowmik P, Zhao B, Rozenzhak S, et al. Chromatographic purification of soluble single-walled carbon nanotubes (s-SWNTs). Journal of the American Chemical Society. 2001;123(4):733-4.

Raffaini G, Ganazzoli F. Protein adsorption on biomaterial and nanomaterial surfaces: a molecular modeling approach to study non-covalent interactions. Journal of Applied Biomaterial and Biomechanics. 2010;8(3):135-45.

Sayes CM, Liang F, Hudson JL, Mendez J, Guo W, Beach JM, et al. Functionalization density dependence of single-walled carbon nanotubes cytotoxicity in vitro. Toxicology letters. 2006;161(2):135-42.

Silverstein et al., Spectrometric identification of organic compounds, 546 Journal of Chemical Education, vol. 39, No. 11, Nov. 1962, 546-553.

Singh B, Saini K, Choudhary V, Teotia S, Pande S, Saini P, et al. Effect of length of carbon nanotubes on electromagnetic interference shielding and mechanical properties of their reinforced epoxy composites. Journal of nanoparticle research. 2014;16(1):1-11.

Tohji K, Takahashi H, Shinoda Y, Shimizu N, Jeyadevan B, Matsuoka I, et al. Purification procedure for single-walled nanotubes. The Journal of Physical Chemistry B. 1997;101(11):1974-8.

Vetcher AA, Srinivasan S, Vetcher IA, Abramov SM, Kozlov M, Baughman RH, et al. Fractionation of SWNT/nucleic acid complexes by agarose gel electrophoresis. Nanotechnology. 2006;17(16):4263-9.

Wang X, Jiang Q, Xu W, Cai W, Inoue Y, Zhu Y. Effect of carbon nanotube length on thermal, electrical and mechanical properties of CNT/bismaleimide composites. Carbon. 2013;53:145-52.

Yamamoto K, Akita S, Nakayama Y. Orientation and purification of carbon nanotubes using ac electrophoresis. Journal of physics D: Applied physics. 1998;31(8):L34-6.

Yao Z, Postma HWC, Balents L, Dekker C. Carbon nanotube intramolecular junctions. Nature. 1999;402(6759):273-6.

(56) References Cited

OTHER PUBLICATIONS

Yudasaka M, Zhang M, Jabs C, Iijima S. Effect of an organic polymer in purification and cutting of single-wall carbon nanotubes. Applied Physics A. 2000;71(4):449-51.

Z. Borzooeian MET, G. Borzooeian, O. Ghasemi, M. Aminlari. Activity and Stability Analysis of Covalent Conjugated Lysozyme-single walled carbon nanotubes: Potential Biomedical and Industrial Applications. RSC Adv., 2017, 7, 48692-48701.

Ziegler KJ, Rauwald U, Gu Z, Liang F, Billups W, Hauge RH, et al. Statistically accurate length measurements of single-walled carbon nanotubes. Journal of nanoscience and nanotechnology. 2007;7(8):pp. 1-5.

Borzooeian et al., "A high precision length-based carbon nanotube ladder," published in RSC Adv. 2018, 8, 36049-36055 (2018).

Borzooeian et al., Preparation and investigation on properties of lysozyme chemically bonded to single-walled carbon nanotubes, Journal of Experimental Nanoscience, 2010 (5), p. 536-47. (Year: 2010).

Brunelle et al., One-dimensional SDS-Polyacrylamide Gel Electrophoresis (1D SDS-PAGE), Methods in Enzymology, 2014(541),Chapter 12, p. 151-59. (Year: 2014).

Du et al., Growth of Carbon Nanotubes by Pyrolysis of Thiophene, 111 Journal of Physical Chemistry, 2007, p. 14293-98. (Year: G.2007).

Usrey et al., Controlling the Electrophoretic Mobility of Single-Walled Carbon Nanotubes: A comparison of Theory and Experiment, 23, Langmuir, 2007, p. 7768-76. (Year: 2007).

Wang et al., "Fabrication of Ultralong and Electrically Uniform Single-Walled Carbon Nanotubes on Clean Substrates", Nano Letter, vol. 9, No. 9, 2 pages (2009).

\* cited by examiner

| Step 1 | Carboxylating a collection of carbon nanotubes. |

| Step 2 | Covalently linking lysozyme to at least a portion of the carboxylated nanotubes. |

| Step 3 | Subjecting the lysozyme-conjugated carbon nanotubes to gel electrophoresis to separate the conjugated carbon nanotubes based on their lengths |

LENGTH-BASED CARBON NANOTUBE LADDERS

RELATED APPLICATION

The present application claims priority to provisional application No. 62/656,645 titled "Length-based carbon nanotube ladders," which was filed on Apr. 12, 2018 and which is herein incorporated by reference in its entirety.

BACKGROUND

The present invention is generally related to methods of determining the distribution of lengths of a collection of carbon nanotube.

Carbon nanotubes (CNTs) of different lengths, diameters and structures are produced using a variety of different methods. Such carbon nanotubes can be employed in a variety of applications, ranging from nano-electronics to semiconductors to probes and interconnects, nanosensors, among others. Geometrical parameters of the carbon nanotubes can have a significant impact on their properties, such as reactivity and conductivity. For example, thermal and electrical conductivities of carbon nanotubes are directly related to their lengths. There is, however, no reliable methods for precise and rapid measurement of lengths of carbon nanotubes.

SUMMARY

In one aspect, a method of determining distribution of lengths of a collection of carbon nanotubes is disclosed, which comprises conjugating a biomolecule to surfaces of at least a portion of the carbon nanotubes, and separating the conjugated carbon nanotubes having different lengths based on their different charge and size-dependent mobilities.

In some embodiments, the conjugation of the biomolecule to the carbon nanotubes can be achieved by carboxylating the carbon nanotubes and covalently linking the conjugated carbon nanotubes to the COOH moieties of the carboxylated carbon nanotubes. In some such embodiments, a linking agent is employed for covalently binding the biomolecule to the surfaces of the carbon nanotubes. By way of example, the linking reagent can be a carbodiimide reagent, such as N-ethyl-N'-(3-(dimethylamino)propyl)carbodiimide.

In some embodiments, the conjugated carbon nanotubes can be subjected to gel electrophoresis to cause their separation. By way example, in some embodiments, the gel electrophoresis can be a polyacrylamide gel electrophoresis. In some such embodiments, silver staining is employed to enhance the separation of the conjugated carbon nanotubes achieved by gel electrophoresis.

In some embodiments, the biomolecule can be protein. In some such embodiments, the biomolecule can be an enzyme. By way of example, the enzyme can lysozyme, such as chicken egg white lysozyme. In some such embodiments, the conjugation of the lysozyme to the carbon nanotubes can be achieved using the carbodiimide method.

In some embodiments, the gel electrophoresis of the conjugated carbon nanotubes results in a plurality of separated bands, each of which corresponds to a particular length of the conjugated carbon nanotubes. In some such embodiments, the intensity of each band can be analyzed to derive a length of the conjugated carbon nanotubes associated with that band. Further, in some embodiments, analyzing an intensity of each band can comprise relating length of carbon nanotubes associated with each band to an intensity of said band according to the following relation:

$$L = d\exp\left[\frac{3\pi\eta\mu}{q(d)e} - 2\ln 2 + 1\right],$$

wherein,
L is the calculated length,
D is mean diameter,
$\eta$ is viscosity,
q(d) is persistence length,
$\mu$ is mobility,
e is the electron charge, and
d is the average diameter of each carbon nanotube.

Further, in some aspects, the value of q(d) can calculated according to Usrey et al. (M. L. Usrey, N. Nair, D. E. Agnew, C. F. Pina and M. S. Strano, Langmuir, 2007, 23, 7768-7776), the teachings of which has been incorporated by reference in its entirety. In some embodiments, $\eta$ can be about 1.25 (Pa·s).

In a related aspect, a method for determining average length of a sample of carbon nanotubes, which comprises labelling each of a plurality of carbon nanotubes with a biological moiety, to provide labelled carbon nanotubes; subjecting the labelled carbon nanotubes to gel electrophoresis, to provide a electrophoresis gel comprising the labelled carbon nanotubes; treating the electrophoresis gel comprising the labelled carbon nanotubes with a visualizing agent to provide stained, labelled carbon nanotubes; and measuring at a plurality of locations in the electrophoresis gel the visual intensity of the stained, labelled carbon nanotubes; wherein the average length of the stained, labelled carbon nanotubes is a function of their distance travelled in the electrophoresis gel.

In some embodiments, the carbon nanotubes can be any of multi-walled or single-walled carbon nanotubes.

BRIEF DESCRIPTION OF THE DRAWINGS

FIG. 1 is a flow chart depicting various steps in a method according to the present teachings for determining the distribution of lengths of a collection of carbon nanotubes.

DETAILED DESCRIPTION

In one aspect, the present invention is generally directed to methods for measuring distribution of lengths of a collection of carbon nanotubes. In particular, the present teachings provide an indicator for length-based separation of carbon nanotubes (CNTs) via conjugation of one or more biomolecules onto the surfaces of the nanotubes. As discussed in more detail below, in some embodiments, such a method can include conjugating a biomolecule to the carbon nanotubes and subject the conjugated carbon nanotubes to silver-stained gel electrophoresis to separate the conjugated carbon nanotubes based on their lengths.

With reference to the flow chart of FIG. 1, in one such embodiment, a collection of carbon nanotubes are carboxylated (step 1), and lysozyme is covalently linked to the carboxylated carbon nanotubes via linkage to their surface COOH moieties (step 2). By way of example, carbodiimide method can be used for bio-conjugation of lysozyme onto surfaces of the carboxylated carbon nanotubes. Subsequently, the conjugated carbon nanotubes are subjected to gel electrophoresis (step 3) to cause separation of the conjugated carbon nanotubes based on their lengths.

Without being limited to any particular theory, lysozyme-conjugated CNTs with different lengths exhibit different mobilities when subject to gel electrophoresis. In particular, covalent attachment of lysozyme to carbon nanotubes can give rise to an intrinsic positive change on any given individual nanotube or bundle of nanotubes, thus affecting their mobilities. In other words, the degree of bioconjugation can affect the separation process and net charge of the carbon nanotubes, thus allowing their separation.

Again without being limited to any particular theory, depending on their length, each conjugated carbon nanotube moves differently through the gel matrix when subjected to electric field. For example, small CNT fragments will experience less resistance when passing through the pores of the gel, while larger ones will experience more resistance. Thus, the conjugated CNTs migrate different distances based on their lengths. In other words, smaller CNTs travel farther down the gel, while larger ones remain closer to the point of loading of the CNTs onto the gel. The velocity (mobility) of the charged CNT fragments is directly proportional to the electric field (E) and the charge of the CNT fragments (q), and inversely proportional to the frictional coefficient of the mass and shape of the fragment (f).

Since the gel acts like a sieve and retains the larger nanotubes while allowing the smaller ones pass through, the frictional coefficient is a representation of the level of resistance that the carbon nanotubes face as they pass through the pores of the gel. As the length of the carbon nanotube is a key factor in its mobility in the gel matrix, one can obtain the following relation: mobility=(voltage)(charge)/(length). In this manner, a ladder of carbon nanotubes can be obtained based on their lengths.

Further understanding of various aspects of the invention can be obtained by reference to Appendix A, which is an article entitled "A high precision length-based carbon nanotube ladder," published in RSC Adv. 2018, 8, 36049-36055 (2018).

Those having ordinary skill in the art will appreciate that various changes can be made to the above embodiments without departing from the scope of the invention.

What is claimed is:

1. A method of determining distribution of lengths of a collection of carbon nanotubes, comprising:
   conjugating a biomolecule to surfaces of at least a portion of the carbon nanotubes,
   separating the conjugated carbon nanotubes having different lengths based on their different charge and size-dependent mobilities,
   wherein said conjugating step comprises carboxylating said carbon nanotubes, and
   wherein said conjugating step further comprises covalently linking said biomolecule to COOH moieties of said carboxylated carbon nanotubes.

2. The method of claim 1, wherein said biomolecule comprises a protein.

3. The method of claim 2, wherein said biomolecule comprises an enzyme.

4. The method of claim 3, wherein said biomolecule comprises lysozyme.

5. The method of claim 4, wherein said lysozyme comprises chicken egg white lysozyme.

6. The method of claim 1, wherein said step of conjugating the biomolecule to said carbon nanotubes comprises covalently linking the biomolecule to surfaces of said carbon nanotubes.

7. The method of claim 6, wherein said covalently linking of the biomolecule to surfaces of said carbon nanotubes is achieved via linking agent.

8. The method of claim 7, wherein said linking agent comprises a carboiimide reagent.

9. The method of claim 8, wherein said carbodiimide reagent is N-ethyl-N'-(3-(dimethylamino)propyl)carbodiimide.

10. The method of claim 1, wherein said step of separating the conjugated carbon nanotubes comprises subjecting said carbon nanotubes to gel electrophoresis.

11. The method of claim 10, wherein said gel electrophoresis comprises a silver-stained gel electrophoresis.

12. The method of claim 11, wherein said gel electrophoresis comprises sodium dodecyl sulfate polyacrylamide gel electrophoresis (SDS-PAGE).

13. A method of determining distribution of lengths of a collection of carbon nanotubes, comprising:
    conjugating a biomolecule to surfaces of at least a portion of the carbon nanotubes,
    separating the conjugated carbon nanotubes having different lengths based on their different charge and size-dependent mobilities,
    wherein said step of separating the conjugated carbon nanotubes comprises subjecting said carbon nanotubes to gel electrophoresis,
    wherein said step of subjecting the conjugated carbon nanotubes to gel electrophoresis separates the conjugated carbon nanotubes into separate bands corresponding to their lengths.

14. The method of claim 13, wherein said carbon nanotubes in each band have substantially similar length.

15. The method of claim 1, wherein said carbon nanotubes comprise single walled carbon nanotubes (SWCNTs).

16. The method of claim 1, wherein said carbon nanotubes comprise multi-walled carbon nanotubes.

17. The method of claim 13, further comprising analyzing an intensity of each band generated by said gel electrophoresis to determine a length of carbon nanotubes associated with said band.

18. The method of claim 17, wherein said step of analyzing an intensity of each band comprises relating length of carbon nanotubes associated with each band to an intensity of said band corresponding to the following relation:

$$L = d\exp\left[\frac{3\pi\eta\mu}{q(d)e} - 2\ln2 + 1\right],$$

wherein,
L is the calculated length,
D is mean diameter,
$\eta$ is viscosity,
q(d) is persistence length,
$\mu$ is mobility,
e is the electron charge, and
d is the average diameter of each carbon nanotube.

19. The method of claim 10, further comprising sonicating said conjugated carbon nanotubes prior to subjecting them to gel electrophoresis.

20. A method of determining average length of a sample of carbon nanotubes, comprising:
    labelling each of a plurality of carbon nanotubes with a biological moiety, to provide labelled carbon nanotubes;

subjecting the labelled carbon nanotubes to gel electrophoresis, to provide an electrophoresis gel comprising the labelled carbon nanotubes;

treating the electrophoresis gel comprising the labelled carbon nanotubes with a visualizing agent to provide stained, labelled carbon nanotubes;

measuring at a plurality of locations in the electrophoresis gel the visual intensity of the stained, labelled carbon nanotubes;

wherein the average length of the stained, labelled carbon nanotubes is a function of their distance travelled in the electrophoresis gel.

21. The method of claim 20, wherein said carbon nanotubes are single-walled carbon nanotubes.

22. The method of claim 20, wherein said carbon nanotubes are multi-walled carbon nanotubes.

23. The method of claim 20, wherein said biological moiety comprises an enzyme.

24. The method of claim 20, wherein said biological moiety comprises lysozyme.

25. The method of claim 24, wherein said lysozyme comprises chicken egg white lysozyme.

26. The method of claim 20, wherein said step of labelling the carbon nanotubes with said biological moiety comprises covalently linking the biological moiety to surfaces of said carbon nanotubes.

27. The method of claim 20, wherein said covalently linking of the biological moiety to surfaces of said carbon nanotubes is achieved via a linking agent.

28. The method of claim 27, wherein said linking agent comprises a carboiimide reagent.

29. The method of claim 28, wherein said carbodiimide reagent is N-ethyl-N'-(3-(dimethylamino)propyl)carbodiimide.

30. The method of claim 20, further comprising analyzing an intensity of each band generated by said gel electrophoresis to determine a length of carbon nanotubes associated with said band.

* * * * *